United States Patent [19]

Kawamoto et al.

[11] 4,331,608
[45] May 25, 1982

[54] LIQUID PHASE CATALYTIC CO-OXIDATION PROCESS

[75] Inventors: Keiji Kawamoto, Hatsukaichi; Toshihiro Yoshioka, Otake, both of Japan

[73] Assignee: Mitsui Petrochemical Industries, Ltd., Tokyo, Japan

[21] Appl. No.: 155,673

[22] Filed: Jun. 2, 1980

[30] Foreign Application Priority Data

Jun. 6, 1979 [JP] Japan .................................. 54/69867
Jun. 26, 1979 [JP] Japan .................................. 54/79628

[51] Int. Cl.³ ............................ C09F 7/02; C11C 3/00
[52] U.S. Cl. .................................... 260/406; 562/408; 562/503; 562/504; 562/543; 562/508; 562/509; 562/544; 562/548; 560/51; 560/55; 560/77; 560/121; 560/127; 560/190; 560/243; 568/431
[58] Field of Search .................. 260/406; 560/51, 55, 560/77, 121, 127, 190, 243; 562/408, 503, 504, 543, 508, 509, 544, 548

[56] References Cited

U.S. PATENT DOCUMENTS

| | | | |
|---|---|---|---|
| 3,409,649 | 11/1968 | Keblys | 260/413 |
| 3,658,896 | 4/1972 | Washecheck | 562/544 |
| 3,668,257 | 6/1972 | Schaeffer | 562/544 |
| 3,821,259 | 6/1974 | Bljumberg et al. | 260/348.5 V |

*Primary Examiner*—John F. Niebling
*Attorney, Agent, or Firm*—Cushman, Darby & Cushman

[57] ABSTRACT

Unsaturated compounds having at least 4 carbon atoms, including unsaturated alicyclic compounds having at least 4 carbon atoms, unsaturated aliphatic compounds having at least one carbon-carbon unsaturated bond and having at least 4 carbon atoms and unsaturated aromatic compounds having at least one carbon-carbon unsaturated bond in the branched chain thereof and (ii) aldehydes or ketones having at least 4 carbon atoms are catalytically co-oxidized with an oxygen-containing gas in a liquid phase to form a cleaveged product or products of unsaturated bond of the unsaturated compounds at a high yield. This co-oxidation reaction is carried out in the presence of a heavy metal containing iron, cobalt, nickel, ruthenium, rhodium, palladium, osmium, iridium, platinum, copper, silver, chromium, molybdenum, tungsten, manganese and rhenium and the compounds thereof.

14 Claims, No Drawings

LIQUID PHASE CATALYTIC CO-OXIDATION PROCESS

The present invention relates to a liquid phase catalytic co-oxidation process. More specifically, it relates to a process for catalytically co-oxidizing (i) unsaturated compounds having at least 4 carbon atoms, such as, unsaturated alicylic compounds having at least 4 carbon atoms, unsaturated aliphatic compounds having at least one carbon-carbon unsaturated bond and having at least 4 carbon atoms and unsaturated aromatic compounds having at least one carbon-carbon unsaturated bond in the branched chain thereof and (ii) aldehydes, or ketones having at least 4 carbon atoms in a liquid phase.

It has been well known heretofore that compounds having an unsaturated bond or bonds are oxidized with appropriate oxidizing agents, such as dichromate compounds, permanganate compounds, nitric acid and the like, whereby organic acids are produced by oxidative cleavage of the unsaturated bond. However, there are disadvantages in these known processes in that at least an equivalent amount of the oxidizing agents must be used in the oxidation reactions and also in that large amounts of wasteful by-products are produced by the oxidation reactions.

It is also known in the art that unsaturated compounds are oxidized with ozone, whereby alcohols, aldehydes, carboxylic acids and the like are produced by oxidative cleavage of the unsaturated bond. However, since this process requires not only special apparatuses, but also complicated post treatments after reaction, this process is not desirable from the practical point of view.

Furthermore, even when unsaturated alicyclic compounds such as cyclohexene, cyclooctene, cyclododecene and the like, or unsaturated aliphatic compounds, such as octene, dodecene, oleic acid and the like are catalytically oxidized in a liquid phase with a gas containing molecular oxygen in the presence of a heavy metal catalyst, only trace amounts of organic carbonyl compounds, such as carboxylic acids, aldehydes, ketones and the like, having a structure derived from oxidative cleavage of the unsaturated bond are produced, but products having a structure derived from the oxidation at the allyl position, such as, hydroperoxides, alcohols, ketones, aldehydes, epoxides or the like are produced.

In addition, Japanese Patent Publication No. 44-5848/69 discloses an oxidation process in which a mixed gas of propylene and acetaldehyde in oxidized with a gas containing molecular oxygen. United States Patent No. 3821259 discloses a co-oxidation process in which propylene and acetaldehyde are co-oxidized with a gas containing molecular oxygen in the presence of a silver catalyst or vanadium catalyst. However, produced in these processes, as main products, are propylene oxide, which is derived from the oxidation of the double bond of propylene, and acetic acid, which is derived from the oxidation of acetaldehyde, and only trace amounts of organic carboxylic acids derived from oxidative cleavage of the double bond of propylene are produced, as a by-product, in these processes.

Accordingly, an object of the present invention is to obviate the afore-mentioned disadvantages of the prior arts and to provide a liquid phase co-oxidation process in which unsaturated compounds including unsaturated alicyclic compounds having at least 4 carbon atoms, unsaturated aliphatic compounds having at least one carbon-carbon unsaturated bond and having at least 4 carbon atoms and unsaturated aromatic compounds having at least one carbon-carbon unsaturated bond in the branched chain thereof are co-oxidized, together with aldehydes, or ketones having at least 4 carbon atoms with a gas containing molecular oxygen, whereby the unsaturated bond of the unsaturated compounds is oxidatively cleaved to form the cleavaged compounds such as carboxylic acids or ketones.

Other objects and advantages of the present invention will be apparent from the description set forth hereinbelow.

In accordance with the present invention, there is provided a process for preparing at least one cleavaged product of the unsaturated bond of an unsaturated compound having at least 4 carbon atoms comprising the step of:

catalytically co-oxidizing (i) the unsaturated compound and (ii) an aldehyde, or a ketone having at least 4 carbon atoms in a liquid phase with a gas containing molecular oxygen in the presence of a catalyst consisting essentially of a heavy metal or the compound thereof.

In the case where an unsaturated alicyclic compound having at least 4 carbon atoms is used, as the unsaturated compound, a corresponding polycarboxylic acid is selectively formed by cleavage of the unsaturated bond of the alicyclic compound.

In the case where an unsaturated aliphatic compound having at least one carbon-carbon unsaturated bond and having at least 4 carbon atoms or an unsaturated aromatic compound having at least one carbon-carbon unsaturated bond in the branched chain thereof, is used, as the unsaturated compound, corresponding organic carbonyl compounds, such as, carboxylic acids and ketones, are selectively formed by cleavage of the carbon-carbon unsaturated bond.

The unsaturated alicyclic compounds employed, as a reactant, in the present invention are those which have at least one carbon-carbon unsaturated bond in the ring of the alicyclic compounds. Typical examples of such compounds are: for example, unsaturated alicyclic hydrocarbons, such as, cyclopentene, cyclopentadiene, dicyclopentadiene, cyclohexene, methylcyclohexene, ethylcyclohexene, vinylcyclohexene, chlorocyclohexene, nitrocyclohexene, methoxycyclohexene, cycloheptene, cyclooctene, cyclooctadiene, cyclodecene, cyclododecene, cyclododecadiene, cyclododecatriene, norbornene and the like; unsaturated alicyclic carboxylic acids or the derives thereof, such as, trans-$\Delta^4$-tetrahydrophthalic acid or its anhydride, cis-$\Delta^4$-tetrahydrophthalic acid or its anhydride and the like; and isophorone, limonene, isolimonene, terpinenes, menthenes, pyronene and the like. Among these unsaturated alicyclic compounds, cyclohexene, cyclododecene, cis-$\Delta^4$-tetrahydrophthalic acid or its anhydride can be preferably used in the present invention.

The unsaturated aliphatic compounds having at least one carbon-carbon unsaturated bond and having at least 4 carbon atoms employed, as one reactant, in the present invention include: for example, unsaturated aliphatic hydrocarbons, such as, butene, butadiene, pentene, pentadiene, hexene, hexadiene, octene, octadiene, octatriene, decene, dodecadiene, dodecatriene and the like; unsaturated aliphatic carboxylic acids or the derivative thereof, such as, acrylic acid, methacrylic acid, α-chloromethyl acrylic acid, α-nitromethyl acrylic acid, hexenoic acid, octenoic acid, itaconic acid, oleinic acid, linolic acid, erucic acid and the esters thereof; other aliphatic compounds having an unsaturated bond or bonds, such as, methyl vinyl ketone, mesityl oxide, isophorone and the like. Among these unsaturated aliphatic compounds, unsaturated aliphatic carboxylic acids having at least 4 carbon atoms or the esters thereof can be preferably used in the present invention. Most preferable aliphatic compounds used in the present invention are methacrylic acid, oleic acid, erucic acid and the esters thereof.

The unsaturated branched aromatic compounds having at least one carbon-carbon unsaturated bond in the branched chain thereof include: for example, unsaturated aromatic hydrocarbons, such as, α-methylstyrene, 3-phenylpropylene, indene, vinylnaphthalene and the like; unsaturated aromatic ether, such as, safrole, isosafrole and the like; unsaturated aromatic carboxylic acids or the esters thereof, such as, atropic acid, 2-phenylpentenoic acid, the esters thereof and the like. Among these unsaturated aromatic compounds, atropic acid and the esters thereof can be preferably used in the present invention.

In the case where the above-mentioned unsaturated aliphatic or aromatic compounds are subjected to the oxidative cleavage reaction, carboxylic acids are formed if hydrogen is bonded to the carbon atom of the unsaturated bond to be cleaved and ketones are formed if hydrogen is not bonded to the carbon atom of the unsaturated bond to be cleaved.

The aldehydes employed, as a co-reactant, in the present invention can be aliphatic, alicyclic or aromatic aldehydes. Typical examples of the aldehydes used in the present invention are, for example, formaldehyde or paraformaldehyde (which can decompose under the reaction condition to form formaldehyde), acetaldehyde, paraldehyde, glyoxal, propionaldehyde, butylaldehyde, benzaldehyde, tolualdehyde, cuminaldehyde and the like.

The ketones having at least 4 carbon atoms employed, as a co-reactant, in the present invention can be aliphatic, alicyclic or aromatic ketones. Typical examples of the ketones used in the present invention are, for example, methyl ethyl ketone, methyl isobutyl ketone, biacetyl, cyclohexanone, methyl benzyl ketone, dibenzyl ketone and the like.

Among these aldehydes and ketones, aldehydes, especially aliphatic and aromatic aldehydes are preferably used in the present invention. Examples of these aldehydes are acetaldehyde, isobutylaldehyde benzaldehyde and tolualdehyde, and acetaldehyde is the most preferable one from the economical point of view. These aldehydes or ketones can be used alone or any combination thereof.

The amount of the aldehydes or ketones used in the present invention is preferably within the range of from 0.1 to 200 mol, more preferably within the range of from 1 to 50 mol, based on 1 mol of the afore-mentioned unsaturated compounds. When the amount of the aldehydes or ketones is less than 0.1 mol based on 1 mol of the unsaturated compounds, the initiation of the reaction is unpreferably retarded and the co-oxidation reaction rate becomes low, so that the yield of the desired products is decreased. Contrary to this, when the amount of the aldehydes or ketones is more than 200 mol based on 1 mol of the unsaturated compounds, undesirable by-products are formed and the yield of the desired products is decreased due to the occurence of vigorous oxidation reactions. Furthermore, the use of a large amount of the co-oxidizing agents, which also requires the use of large reaction apparatus, is not preferable from the economical point of view.

The liquid phase co-oxidation reaction of the present invention is carried out in the presence of a heavy metal catalyst. The term "a heavy metal catalyst" as used herein means a catalyst consisting essentially of a heavy metal and the compound thereof. Typical examples of heavy metals used, as a catalyst, in the present invention are iron, cobalt, nickel, ruthenium, rhodium, palladium, osmium, iridium, platinum, copper, silver, chromium, molybdenum, tungsten, manganese and rhenium. The compounds of the heavy metals used, as a catalyst, in the present invention can be any inorganic salts, any organic acid salts and any inorganic or organic complexes. These heavy metal catalysts can be used alone or in any combination thereof.

Among the heavy metal catalysts, metals of the Group VIII of the Periodic Table or the compounds thereof can be preferably used in the present invention. Preferable catalysts are ruthenium, osmium and the compounds thereof. The most preferable catalysts are ruthenium catalysts. Examples of the ruthenium catalyst are: ruthenium metal; ruthenium oxides, such as, ruthenium (III) oxide ($Ru_2O_3$), ruthenium (IV) oxide ($RuO_2$), ruthenium (VIII) oxide ($RuO_4$) and the like; ruthenium oxide; ruthenium halides, such as, ruthenium chloride, ruthenium bromide, ruthenium iodide and the like; ruthenium sulfate; various ruthenium complexes; and the like. Especially when the ruthenium catalysts are used, cobalt, iron, manganese, chromium, copper or the compounds thereof are preferably used, in combination with the ruthenium catalyst, to improve the catalytic activity. The use of cobalt, iron or the compounds thereof, in combination with the ruthenium catalysts, are most preferable.

The heavy metal catalysts can be used in an amount of from 0.0001 to 1, more preferably 0.001 to 0.01 gram atom, in terms of a heavy metal atom, based on 1 mol of the afore-mentioned unsaturated compounds. When the amount of the heavy metal catalysts is less than 0.0001 gram atom, in terms of a heavy metal atom, based on 1 mol of the unsaturated compounds, relatively large amounts of epoxides and diols are formed, so that the yield of the desired products is unpreferably decreased. Contrary to this, when the amount of the heavy metal catalysts is more than 1 gram atom, the co-oxidation reaction is unpreferably retarded, so that relatively long reaction time is required. Furthermore, the use of the relatively large amount of the catalysts naturally causes the increase in the loss of the catalysts when the used catalysts are recovered. In the case where the ruthenium catalysts are used, together with the above mentioned other heavy metal catalyst components (e.g. Co, Fe, Mn, Cr, Cu or the compounds thereof), in the present invention, the amount of the other heavy metal catalyst components is preferably within the range of from 0.000001 to 0.1 gram atom, more preferably, within the range of from 0.00001 to 0.01 gram atom, in terms of the heavy metals, based on 1 mol of the above-mentioned unsaturated compounds and is preferably within the range of from 0.0001 to 10 gram atom, more preferably 0.001 to 1 gram atom, in terms of the heavy metal, based on 1 gram atom of the ruthenium contained in the ruthenium catalyst.

The liquid phase catalytic co-oxidation reaction of the present invention is carried out by contacting the afore-mentioned reactants with a gas containing molecular oxygen. Examples of a gas containing molecular oxygen used in the present invention are oxygen, air, a mixed gas of oxygen and an inert gas, such as nitrogen having an appropriate oxygen content. Among these gases, air is usually used. The amount of the oxygen used in the present invention is not critical, so long as oxygen is present in the reaction system.

Although the liquid phase catalytic co-oxidation reaction of the present invention is generally carried out in the presence of appropriate solvents, the reaction can be carried out in the absence of a solvent. The solvents used in the present invention can be any solvent which is inert or inactive to the co-oxidation reaction. Examples of the solvents used in the present invention are: halogenated hydrocarbons, such as, carbon tetrachloride, chloroform, methylene chloride, methyl chloride, ethylene chloride, dichloroethane, dichlorobenzene and the like; aliphatic or alicyclic hydrocarbons, such as pentane, hexane, heptane, octane, cyclohexane and the like; aromatic compounds, such as, benzene, toluene, xylene, nitrobenzene and the like; esters, such as, ethyl acetate, methyl benzoate, phenyl acetate and the like; carboxylic acids, such as, acetic acid, propionic acid, butyric acid and the like; compounds having ether linkage, such as, diethyl ether, dioxane, tetrahydrofuran and the like; methanol; acetone; and the like. Optionally, the co-oxidation reaction can be carried out in the presence of water. Among these solvents, acetone, ethyl acetate, acetic acid, methanol and dioxane can be preferably used in the present invention.

In the case where the afore-mentioned heavy metal catalysts are insoluble in organic solvents, these catalysts can be used by dissolving in water. Mixed solvents of water and an organic solvent or solvents can also be used. When heterogeneous mixed solvents of water and water-insoluble organic solvents are used, the co-oxidation reaction can be carried out with good agitation.

The liquid-phase catalytic co-oxidation reaction of the present invention can be batchwise or continuously carried out by contacting a mixture of (a) the afore-mentioned unsaturated compounds, (b) the aldehydes or ketones, (c) the heavy metal catalysts and (d), optionally, the solvents with a gas containing molecular oxygen under stirring. The reaction temperature is generally within the range of from 0° to 200° C., preferably within the range of from 20° to 150° C. The present co-oxidation reaction can be carried out under an atomspheric pressure and an elevated pressure. The reaction period of time can be varied over a wide range, depending upon the reaction temperature and other reaction conditions. Furthermore, in order to accelerate the oxidation of the aldehydes or the ketones in the present co-oxidation reaction, aromatic carboxylic acids and alifatic carboxylic acids, such as pyromellitic acid, trimellitic acid, citric acid, acetylene dicarboxylic acid and oxalacetic acid can be added to the reaction mixture. In the case where these aromatic carboxylic acids are used, the preferable amount thereof is within the range of from 0.00001 to 0.01 mol, based on 1 mol of the aldehydes or the ketones.

The co-oxidation reaction products (e.g. polycarboxylic acid, carboxylic acids, ketones) can be recovered from the reaction mixture by, for example, distillation, extraction or crystallization in any known manner. When the co-oxidation reaction is carried out in an alcohol solvent, there is the possibility that the resultant carboxylic acids are obtained in the form of the ester. In addition, according to the present invention, simultaneously with the formation of the polycarboxylic acids or the organic carbonyl compounds (e.g. ketones, carboxylic acids) derived from the oxidative cleavage of the unsaturated compounds, organic acids derived from the oxidation of the ketones or aldehydes are also produced. These organic acids can also be recovered from the reaction products in any known manner.

The present invention will be further illustrated by, but is by no means limited to, the following examples in which all yield percentages are expressed on a molar basis unless otherwise noted.

EXAMPLE 1

A solution containing 12 g of acetaldehyde, 0.03 g of pyromellic acid, 0.085 g of $RuO_2.2H_2O$ and 96 g of acetone was placed in a reactor provided with a reflux condenser and heated to a temperature of 40° C. 20 liter/hr of oxygen was passed into the solution to initiate the reaction. The reflux condenser was cooled to a temperature of $-40°$ C. and unreacted acetaldehyde was refluxed. After reaction was carried out for 30 minutes, a solution of 1.52 g of cis-$\Delta^4$-tetrahydrophthalic anhydride and 20 g of acetone was dropwise added to the reaction mixture over one hour. After the dropwise addition, the reaction was carried out for a further 1.5 hours at a temperature of 40° C. After the completion of the reaction, the reaction mixture was analyzed by gas chromatography. As a result, it was found that acetic acid was obtained at a yield of 96%.

Furthermore, after the catalyst was removed from the reaction mixture by filtration, 75 ml of water was added to the reaction mixture and the hydrolysis reaction was carried out for 2 hours at a temperature of 55° C. After that, the reaction mixture was concentrated under a reduced pressure and the carboxylic acid component was esterified. It was found, by a gas chromatography analysis, that 1,2,3,4-tetracarboxybutane was obtained at a yield of 92%.

EXAMPLE 2

The co-oxidation reaction was carried out in a manner as described in Example 1, except that $RuO_4$ was used in lieu of $RuO_2.2H_2O$. The yield of acetic acid was 95% and the yield of 1,2,3,4,-tetracarboxybutane was 94%.

EXAMPLE 3

The co-oxidation reaction was carried out in a manner as described in Example 1, except that cyclododecene was used in lieu of cis-$\Delta^4$-tetrahydrophthalic anhydride. Acetic acid was obtained at a yield of 95% and 1,10-dicarboxy decane was obtained at a yield of 94%.

EXAMPLE 4

The co-oxidation reaction was carried out in a manner as described in Example 1, except that isobutyl aldehyde was used in lieu of acetaldehyde. Isobutyric acid was obtained at a yield of 93% and 1,2,3,4,-tetracarboxy butane was obtained at a yield of 90%.

COMPARATIVE EXAMPLE 1

Cis-$\Delta^4$-tetrahydrophthalic anhydride was oxidized in a manner as described in Example 1, except that acetaldehyde was not used. As a result, the conversion was 5% and the formation of 1,2,3,4,-tetracarboxy butane was not detected.

COMPARATIVE EXAMPLE 2

The reaction of Example 1 was repeated, except that $RuO_2.2H_2O$ was not used. As a result, although acetic acid was obtained at a yield of 95%, 1,2,3,4,-tetracarboxy butane was not formed.

EXAMPLE 5

A solution containing 6 g of acetaldehyde, 1.5 g of cis-$\Delta^4$-tetrahydrophthalic anhydride, 0.03 g of pyromellitic acid, 0.1 g of $RuO_2.2H_2O$, 50 ml of acetone and 50 ml of ethyl acetate was placed in a 500 ml titanium lined autoclave and provided with a reflux condenser. The autoclave was pressurized with nitrogen to a pressure of 30 kg/cm$^2$G and, then, heated to a temperature of 40° C. A mixed gas containing oxygen and nitrogen at a ratio of 8:92 was introduced into the autoclave at a rate of 100 liter/hr, while the contents of the autoclave having a temperature of 40° C. were stirred at 1500 rpm. Thus, the reaction was started.

After the oxygen content in the effluent gas from the autoclave was decreased to 1% by volume, an additional solution of 18 g of acetaldehyde, 3.1 g of cis-$\Delta^4$-tetrahydrophthalic anhydride and 20 ml of acetone was added to the autoclave over 30 minutes, while the flow rate of the mixed gas was adjusted to such an amount that the oxygen content in the effluent gas was 3% by volume. 10 minutes after the addition of the additional solution, the oxygen content in the effluent gas reached almost 8% by volume. After that, the mixed gas was introduced into the autoclave for a further one hour at a rate of 100 liter/hr.

After the completion of the reaction, the reaction mixture was analyzed by gas chromatography. As a result, it was found that the yield of acetic acid was 93%.

Furthermore, after the catalyst was removed from the reaction mixture by filtration, 75 ml of water was added to the reaction mixture and the hydrolysis reaction was carried out for 2 hours at a temperature of 55° C. After that, the reaction mixture was concentrated under a reduced pressure and the carboxylic acid component was esterified. It was found, by a gas chromatography analysis, that 1,2,3,4-tetracarboxybutane was obtained at a yield of 64%.

EXAMPLE 6

The co-oxidation reaction was carried out in a manner as described in Example 5, except that 3 ppm of cobalt naphthenate was included in the solution first placed in the autoclave. As a result, the yield of acetic acid was 96% and the yield of 1,2,3,4-tetracarboxybutane was 83%.

EXAMPLE 7 THROUGH 14

The co-oxidation reactions were carried out in a manner as described in Example 6, except that various alicyclic olefins listed in Table 1 below were used in lieu of cis-$\Delta^4$-tetrahydrophthalic anhydride. The results are shown in Table 1 below.

TABLE 1

| Example No. | Olefin Compound | Formed Cleavaged Products (Yield) | | Yield(%) of Total Cleavaged Products | Yield (%) of Acetic Acid |
|---|---|---|---|---|---|
| 7 | (Cyclohexene) | C—C—C—C with COOH, COOH (91%) | C—C—C—C with COOH, CHO (4%) | 95 | 94 |
| 8 | (4-Methyl-1-Cyclohexene) | C—C(CH₃)—C—C—C with COOH, COOH (92%); C—C(CH₃)—C—C—C with COOH, CHO (1%) | C—C(CH₃)—C—C—C with CHO, COOH (3%) | 96 | 94 |
| 9 | (3-Methyl-1-Cyclohexene) | C—C—C—C—C with CH₃, COOH, COOH (94%); C—C—C—C—C with COOH, CHO (1%) | C—C—C—C—C with CH₃, CHO, COOH (2%) | 97 | 95 |
| 10 | ($\Delta^3$-Tetrahydrophthalic Acid) | C—C—C—C with COOH, COOH, COOH, COOH (95%) | C—C—C—C with COOH, COOH, COOH, CHO (2%) | 97 | 93 |

TABLE 1-continued

| Example No. | Olefin Compound | Formed Cleavaged Products (Yield) | | Yield(%) of Total Cleavaged Products | Yield (%) of Acetic Acid |
|---|---|---|---|---|---|
| 11 | 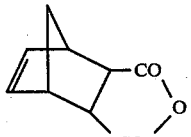 (5-Bicyclo[2,2,1]Heptene-2,3-Dicarboxylic Acid Anhydride) | COOH—[ring]—COOH, COOH (60%) | COOH—[ring]—COOH, CHO (13%) | 73 | 93 |
| 12 | (5-Bicyclo[2,2,1]Heptene-2,3-Dicarboxylic Acid) with COOH, COOH | COOH—[ring]—COOH, COOH (52%) | COOH—[ring]—COOH, COOH (21%) | 73 | 93 |
| 13 | (Norbornene) | COOH—[ring]—COOH (79%) | CHO—[ring]—COOH (11%) | 90 | 93 |
| 14 | (Cyclopentene) | HOOC—C—C—C—COOH (92%) HOOC—C—C—C—CHO (3%) | | 95 | 94 |

EXAMPLE 15

The co-oxidation reaction was carried out in a manner as described in Example 6, except that cyclopentadiene was used in lieu of cis-$\Delta^4$-tetrahydrophthalic anhydride. The yield of acetic acid was 92% and the yields of malonic acid and oxalic acid were 67% and 65%, respectively.

EXAMPLE 16

A solution containing 12 g of acetaldehyde, 0.03 g of pyromellitic acid, 0.085 g of $RuO_2.2H_2O$ and 96 g of acetone was placed in a reactor provided with a reflux condenser and heated to a temperature of 40° C. 20 liter/hr of oxygen was passed into the solution to initiate the reaction. The reflux condenser was cooled to a temperature of −40° C. and unreacted acetaldehyde was refluxed. After reaction was carried out for 30 minutes, a solution of 2.8 g of oleic acid and 20 g of acetone was dropwise added to the reaction mixture over one hour. After the dropwise addition, the reaction was carried out for a further 1.5 hours at a temperature of 40° C. After the completion of the reaction, the reaction mixture was analyzed by gas chromatography. As a result, it was found that acetic acid was obtained at a yield of 96%.

Furthermore, after the catalyst was removed from the reaction mixture by filtration, the reaction mixture was concentrated under a reduced pressure and the carboxylic acid component was esterified. It was found, by a gas chromatography analysis, that azelaic acid and pelargonic acid were obtained at yields of 95% and 92%, respectively.

EXAMPLE 17

The co-oxidation reaction was carried out in a manner as described in Example 16, except that methyl methacrylate was used in lieu of oleic acid. As a result, acetic acid was obtained at a yield of 95% and methyl pyruvate was obtained at a yield of 90%.

EXAMPLE 18

The co-oxidation reaction was carried out in manner as described in Example 16, except that methyl atropate was used in lieu of oleic acid. As a result, acetic acid was obtained at a yield of 95% and methyl benzoylformate was obtained at a yield of 88%.

EXAMPLE 19

The co-oxidation reaction was carried out in a manner as described in Example 16, except that isobutyl aldehyde was used in lieu of acetaldehyde. Isobutyric acid was obtained at a yield of 93% and azelaic acid and peralgonic acid were obtained at yields of 90% and 92%, respectively.

COMPARATIVE EXAMPLE 3

Oleic acid was oxidized in a manner as described in Example 16, except that acetaldehyde was not used. As a result, the conversion was 5% and azelaic acid and peralgonic acid were not detected.

COMPARATIVE EXAMPLE 4

The reaction of Example 16 was repeated, except that $RuO_2.2H_2O$ was not used. As a result, although acetic acid was obtained at a yield of 95%, azelaic acid and peralgonic acid were not detected.

EXAMPLE 20

A solution containing 6 g of acetaldehyde, 1 g of methyl methacrylate, 0.03 g of pyromellitic acid, 0.1 g of $RuO_2 \cdot 2H_2O$, 50 ml of acetone and 50 ml of ethyl acetate was placed in a 500 ml titanium lined autoclave and provided with a reflux condenser. The autoclave was pressurized with nitrogen to a pressure of 30 $kg/cm^2G$ and, then, heated to a temperature of 40° C. A mixed gas containing oxygen and nitrogen at a ratio of 8:92 was introduced into the autoclave at a rate of 100 liter/hr, while the contents of the autoclave having a temperature of 40° C. were stirred at 1500 rpm. Thus, the reaction was started.

After the oxygen content in the effluent gas from the autoclave was decreased to 1% by volume, an additional solution of 18 g of acetaldehyde, 2 g of methyl methacrylate and 20 ml of acetone was added to the autoclave over 30 minutes, while the flow rate of the mixed gas was adjusted to such an amount that the oxygen content in the effluent gas was 3% by volume. 10 minutes after the addition of the additional solution, the oxygen content in the effluent gas reached almost 8% by volume. After that, the mixed gas was introduced into the autoclave for a further one hour at a rate of 100 liter/hr.

After the completion of the reaction, the reaction mixture was analyzed by was chromatography. As a result, it was found that acetic acid was obtained at a yield of 93% and methyl pyruvate was obtained at a yield of 70%.

EXAMPLE 21

The co-oxidation reaction was carried out in a manner as described in Example 20, except that 3 ppm of cobalt naphthenate was included in the solution first placed in the autoclave. As a result, the yield of acetic acid was 97% and methyl pyruvate was quantitatively obtained.

EXAMPLE 22

The co-oxidation reaction was carried out in a manner as described in Example 21, except that octene-1 was used in lieu of methyl methacrylate. Acetic acid was obtained at a yield of 90% and heptyl acid (i.e. enanthic acid) was obtained at a yield of 72%.

EXAMPLE 23 THROUGH 26

The co-oxidation reactions were carried out in a manner as described in Example 21, except that the aromatic unsaturated compounds listed in Table 2 below were used. The results are shown in Table 2 below.

TABLE 2

| Example No. | Olefin compound | Formed Carboxylic Cleavaged Products (Yield) | | Yield(%) of Total Cleavaged Products | Yield(%) of Acetic Acid |
|---|---|---|---|---|---|
| 23 | Ph–CH=CH₂ | Ph–COOH (92%) | Ph–CHO (3%) | 95 | 95 |
| 24 | H₃CO–Ph–CH=CH₂ | H₃CO–Ph–COOH (93%) | H₃CO–Ph–CHO (3%) | 96 | 94 |
| 25 | Ph–CH=CH–Ph | Ph–COOH (82%) | Ph–CHO (5%) | 87 | 92 |
| 26 | Cl–Ph–CH=CH₂ | Cl–Ph–COOH (79%) | Cl–Ph–COOH (5%) | 84 | 92 |

What we claim is:

1. A process for preparing at least one cleavaged product of the unsaturated bond of an unsaturated compound having at least 4 carbon atoms, said process comprising the step of:
catalytically co-oxidizing (i) said unsaturated compound and (ii) an aldehyde in a liquid phase with a molecular oxygen-containing gas in the presence of a catalyst consisting essentially of ruthenium metal or a compound thereof, said aldehyde being present in the starting reaction mixture.

2. The process as claimed in claim 1, wherein the amount of the catalyst, in terms of ruthenium metal atom, is within the range of from 0.001 to 0.1 gram atom, based on 1 mol of the unsaturated compound.

3. The process as claimed in claim 1, wherein the amount of the aldehyde is within the range of from 0.1 to 200 mol, based on 1 mol of the unsaturated compound.

4. The process as claimed in claim 1, wherein the aldehyde is acetaldehyde, isobutyl aldehyde, benzaldehyde or tolualdehyde.

5. The process as claimed in claim 1, wherein the co-oxidation is carried out at a temperature within the range of from 20° to 150° C.

6. The process as claimed in claim 1, 2, 3, 4 or 5, wherein an unsaturated alicyclic compound having at least 4 carbon atoms is used as the unsaturated compound, whereby a corresponding polycarboxylic acid is formed, as the cleavaged product, by cleavage of the unsaturated bond of the alicyclic compound.

7. The process as claimed in claim 6, wherein said alicyclic compound is selected from unsaturated alicyclic hydrocarbons, unsaturated alicyclic carboxylic acids and the derivatives thereof.

8. The process as claimed in claim 6, wherein said alicyclic compound is cyclododecene or cis-$\Delta^4$-tetrahydrophthalic anhydride.

9. The process as claimed in claim 1, 2, 3, 4 or 5, wherein as the unsaturated compound, an unsaturated aliphatic compound having at least one carbon-carbon unsaturated bond and having at least 4 carbon atoms or an unsaturated aromatic compound having at least one carbon-carbon unsaturated bond in the branched chain thereof is used, whereby corresponding organic carbonyl compounds are formed, as the cleavaged product, by cleavage of the carbon-carbon unsaturated bond.

10. The process as claimed in claim 9, wherein said unsaturated aliphatic compound is selected from unsaturated aliphatic hydrocarbons, unsaturated aliphatic carboxylic acids and the derivatives thereof.

11. The process as claimed in claim 10, wherein said unsaturated aliphatic compound is selected from methacrylic acid and its esters, oleic acid and its esters and erucic acid and its esters.

12. The process as claimed in claim 9, wherein said aromatic compound is selected from unsaturated aromatic hydrocarbons, unsaturated aromatic ethers and unsaturated aromatic carboxylic acids and the esters thereof.

13. The process as claimed in claim 12, wherein said aromatic compound is selected from atropic acid and its esters.

14. A process for preparing at least one cleavaged product of the unsaturated bond of an unsaturated compound having at least 4 carbon atoms, said process comprising the step of:

catalytically co-oxidizing a starting reaction mixture of (i) said unsaturated compound and (ii) 0.1 to 200 mol, based on 1 mol of said unsaturated compound, of an aldehyde in a liquid phase with a molecular oxygen-containing gas in the presence of 0.001 to 0.1 gram atom, in terms of ruthenium metal, based on 1 mol of the unsaturated compound, of a catalyst consisting essentially of ruthenium metal or a compound thereof, said co-oxidation conducted at a temperature of 20° to 150° C.

* * * * *